United States Patent

Mracna et al.

[11] Patent Number: 6,015,399
[45] Date of Patent: Jan. 18, 2000

[54] OSTOMY PATIENT EQUIPMENT

[76] Inventors: Kellie Mracna, 1637 Pontiac, SE; Hans Butterwegge, 1637 Pontiac, both of Grand Rapids, Mich. 49506

[21] Appl. No.: 08/831,226

[22] Filed: Apr. 2, 1997

Related U.S. Application Data

[60] Provisional application No. 60/014,780, Apr. 3, 1996, abandoned.

[51] Int. Cl.[7] .................................................... A61F 5/44
[52] U.S. Cl. .......................................... 604/332; 604/334
[58] Field of Search ....................................... 604/332–345

[56] References Cited

U.S. PATENT DOCUMENTS

| | | |
|---|---|---|
| 2,555,086 | 5/1951 | Guinn . |
| 2,679,248 | 5/1954 | Fullaway . |
| 3,019,127 | 1/1962 | Czerwonka et al. . |
| 3,315,447 | 4/1967 | Meier . |
| 3,439,677 | 4/1969 | Bonfils . |
| 3,439,679 | 4/1969 | Doolittle . |
| 3,575,170 | 4/1971 | Clark . |
| 3,759,260 | 9/1973 | Nolan et al. . |
| 3,804,091 | 4/1974 | Nolan et al. . |
| 3,865,109 | 2/1975 | Elmore et al. . |
| 3,952,727 | 4/1976 | Nolan . |
| 3,960,771 | 6/1976 | Tanaka et al. . |
| 3,998,255 | 12/1976 | Mather et al. . |
| 4,160,059 | 7/1979 | Samejima . |
| 4,203,445 | 5/1980 | Jessup et al. . |
| 4,268,286 | 5/1981 | Steer et al. ................................ 604/333 |
| 4,274,848 | 6/1981 | La Gro . |
| 4,863,447 | 9/1989 | Smith ....................................... 604/335 |
| 5,167,650 | 12/1992 | Johnsen et al. ........................... 604/332 |
| 5,372,594 | 12/1994 | Colacello et al. ........................ 604/333 |
| 5,593,397 | 1/1997 | La Gro ..................................... 604/335 |
| 5,658,266 | 8/1997 | Colacello et al. ........................ 604/333 |
| 5,658,267 | 8/1997 | Colacello et al. ........................ 604/333 |
| 5,683,372 | 11/1997 | Colacello et al. ........................ 604/333 |
| 5,840,073 | 11/1998 | Olsen ....................................... 604/333 |

FOREIGN PATENT DOCUMENTS

171343B1  9/1996  Denmark .

*Primary Examiner*—John G. Weiss
*Assistant Examiner*—Dennis Ruhl
*Attorney, Agent, or Firm*—Water and Morse, P.C.

[57] ABSTRACT

A vented colostomy pouch includes a water proof bag having a waste aperture and a vent aperture, with an annular member being secured to the vent aperture and a plug type closure being removably connectable to the annular member to seal the vent opening. The plug and annular member are integrally formed as a unitary member from a plastic material with a flexible attachment interconnecting the annular member and plug. The attachment is deflectable to permit the plug to be inserted and removed from the annular member. The plug has cylindrical side walls that resiliently fit into mating sidewalls in the annular member, with sidewall friction being sufficient to prevent dislodgment without manually moving the plug. The plug is at least slightly longer than the annular member so that the plug clears the opening in the annular member when fully inserted.

18 Claims, 1 Drawing Sheet

OSTOMY PATIENT EQUIPMENT

This application claims priority under U.S.C. 119(e) to provisional application Ser. No. 60/014,780, filed Apr. 3, 1996, now abandoned.

BACKGROUND OF THE INVENTION

This invention relates to ostomy products, i.e., appliances and apparatus to be used by colostomy patients. Medical patients who have contracted colon disease such as cancer must frequently undergo radical colostomy surgery, which results in removal of a substantial amount of the lower intestine and resulting formation of a surgically implemented waste outlet through the abdominal wall, called a "stoma." Such patients must then wear a specially designed pouch-like container, typically of thin, flexible plastic sheet material, which mounts over the stoma to receive and collect body eliminations. Typically, this pouch is releasably attached to a patch-like mounting member called the "appliance," which is adhesively secured to the patient in a secure manner over the stoma and has an opening communicating with the latter. Usually, the patient-mounted "appliance" has a ring-like attachment member, and the pouch has a complementary ring-like portion defining a pair of spaced annular walls which snap over the ring on the appliance to thereby secure the pouch to the appliance in a leak-proof manner. Each such ring-like member has a large central aperture through which eliminated body waste passes to enter the pouch.

One problem which arises in use of such apparatus is the accumulation of gas within the pouch, which inflates the latter in an undesirable manner and may cause leakage or even rupture, etc. The basic practice for dealing with this problem is for the user to retire to a place of privacy and partially disengage the attachment ring, allowing the gas to escape. This is inconvenient and may occasionally cause inadvertent and undesirable spills; furthermore, it also risks unexpected complete separation of the attachment rings, with corresponding detachment of the pouch and probable spilling of its contents. In order to improve on this situation, various vents have been proposed for the pouch, usually in the form of an air filter of one type or another, often incorporating activated charcoal for absorbing odors, permanently or otherwise mounted over a vent opening located somewhere in the top portion of the pouch. Supposedly, such vent filters allow the interior of the pouch to continuously communicate with the exterior through the filter, such that any gas accumulation may automatically pass outward through the filter as function of pressure differentials. In actual practice, however, such filters have experienced substantial difficulty and lack of success, since they often become clogged from the materials inside the pouch, and thus rendered inoperative, leaving the user with no alternative but the old conventional one indicated above. In other instances, such filters have sometimes leaked fluid through them from the inside, causing obviously undesirable results, or else they have simply not been effective or reliable in permitting passage of the accumulated gas outwardly.

Accordingly, colostomy patients continue to experience the basic underlying difficulty and associated problems, giving rise to a continuing need for an ostomy pouch having a truly reliable and effective vent device.

BRIEF SUMMARY OF THE INVENTION

The present invention provides a reliable and effective vent device for ostomy pouches, to satisfy the continuing need referred to above. The invention recognizes that in this environment the air filters described above are unlikely to provide satisfactory operation over any appreciable course of time, and thereby eliminates such filters. Further, the invention recognizes that colostomy patients, like other people, have access to places of privacy, where such intimate, personal matters may be attended to when and as they arise, if only a suitable and convenient means is provided, such that continuously operative filter devices are unnecessary in any event, in a strict sense.

Accordingly, the present invention provides a vent apparatus for a colostomy pouch, which may be attached by the user to conventional ventless colostomy pouches or installed by manufacturers as part of the pouch in the first instance, prior to sale. In a preferred embodiment, such apparatus comprises an open-centered generally annular member securable to one side of the pouch over an aperture extending through that side, to generally encircle such aperture, together with a plug-type closure member releasably and removably receivable within the annular member to seal the vent opening otherwise provided therethrough, such that periodic removal of the plug-type closure member vents the interior of the colostomy pouch through the opening and annular member, and replacement of the closure member reseals the opening. In a particular preferred embodiment, the vent device comprises a one-piece molded member of resilient polymeric material or the like, with one end carrying the annular member and having a flared surrounding skirt-like base which forms an attachment member for the apparatus. In addition, the preferred one-piece member includes a strap-like portion extending from the annular member and carrying the plug-like closure at a distance therefrom, with a living hinge section disposed therebetween by which the closure member may be moved toward and engaged with the annular member, for releasable attachment therein. A further preferred feature of note is an extension or extended part of the plug-type closure member, by which any accumulation of material within the pouch tending to obscure and obstruct the vent opening will automatically be dislodged, and the opening cleared for use.

BRIEF DESCRIPTION OF THE DRAWINGS

The nature of the invention and the more particular aspects of the preferred embodiment disclosed herein will become more apparent following consideration of the ensuing specification and consideration of the attached drawings, in which.

DESCRIPTION OF PREFERRED EMBODIMENT

Figure 1:
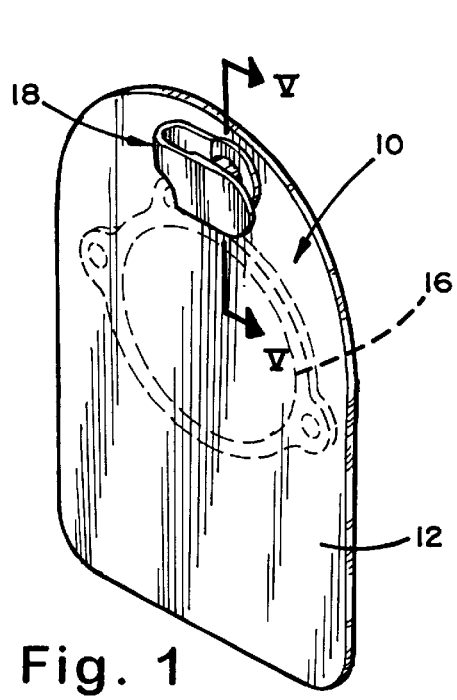
FIG. 1 is a perspective view showing the front and one side of a typical colostomy pouch, showing the vent structure of the invention secured in place thereon.
Figure 2:
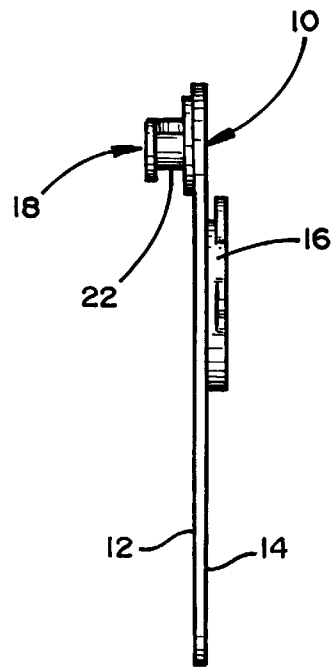
FIG. 2 is a side elevational view of the structure shown in FIG. 1.

Referring now in more detail to the drawings, a typical colostomy pouch 10 is somewhat figuratively shown in FIGS. 1 and 2 for purposes of illustration, the basic nature of such devices being well known and particular examples varying in at least minor details from one manufacturer to another. Generally speaking, however, such devices comprise an envelope-like enclosure made from thin, lightweight plastic material and having a pair of opposite sides 12, 14 which are secured together around their perimeter to form a leak-proof container. As noted above, these devices typically include a ring-like attachment member by which they are secured to the appliance member adhesively attached to the wearer, and such a ring-like member, designated by the numeral 16, is illustrated in FIGS. 1 and 2 for the sake of completeness even though not specifically a part of this invention.

Figure 3:
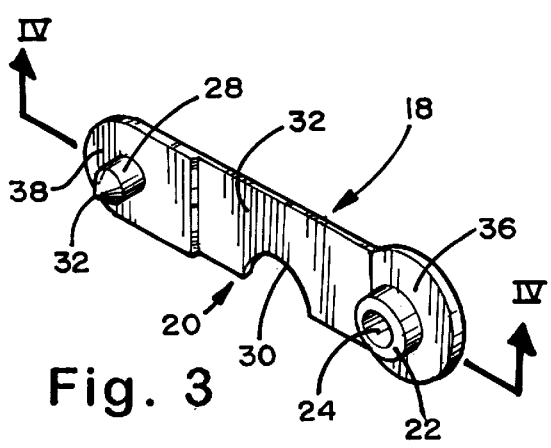
FIG. 3 is a perspective view showing the vent structure of the invention apart from the colostomy pouch and in an open position.

A preferred vent device 18 in accordance with the invention is shown in FIGS. 1 and 2 in an attached position upon the pouch 10, in a desired location (i.e., in the upper portion, preferably above the ring-like attachment member 16). The particular structural nature of a preferred embodiment of the vent 18 is better illustrated in FIGS. 3 and 4, which show that this device is preferably an integrally molded, elongated one-piece member of basically strip-like form having a narrowed-down "living hinge" section 20 generally centrally thereof to facilitate easy and resilient bending into the U-shaped configuration illustrated in FIGS. 1 and 2, in which the vent is closed. Further, the vent device 18 includes an annular and generally tubular vent projection 22 having an open central passage 24 for communication into the interior of the pouch (i.e., the space between sides 12 and 14) through an aperture 26 (FIG. 5) formed in pouch side 12. At its end opposite annular member 22, the vent device 18 includes a plug-like closure member 28 which is insertable into and releasably retained within passage 24 of annular member 22 (FIG. 5), to close the vent opening in a secure, sealed manner. Preferably, the entire one-piece vent member 18 is integrally molded from a resilient, or at least stiffly resilient, polymer such as polyethylene, which not only enables it to be readily flexed into the U-shaped configuration it occupies in a closed condition, but also enables the tubular vent projection 22 and the plug-like closure member 28 to resiliently flex diametrically at least slightly when engaged in the closed position, thereby helping to ensure positive retention of the closure projection within the tubular vent extension.

While various embodiments of a living hinge section 20 may be utilized, the preferred one illustrated includes a generally semicircular cutout or recess 30 formed in a section 32 of reduced cross section, each such feature contributing to the ready flexibility of the hinge section and extending the resulting mechanical stress over a larger area to reduce stress concentration and potential fracture where the resilient bending occurs. Once again, however, these particular attributes are preferred features, and not essential to the invention per se.

Additional preferred features of the invention include a pointed projection 34 at the end of the plug-like closure member 28 (FIGS. 3, 4 and 5), which functions as a clean-out device as noted further below, together with an enlarged, generally circular skirt portion 36 surrounding the tubular projection 22. Skirt portion 36 provides an attachment base by which the vent device 18 may readily be secured to side 12 of pouch 10, over and in alignment with its aperture 26. This may be accomplished either at the time of manufacture or subsequently, by the user, who may also form the aperture 26 as part of the vent installation procedure, in instances where the manufacturer does not provide the vent or the aperture. In cases of such user-application, the vent is readily secured in place to the side of the pouch by use of adhesive (e.g., double-sided adhesive tape) between the pouch and the skirt portion 36, to form either a permanent or releasable connection thereto (releasable connections permitting reuse of the vent device on different pouches). In manufacturer-installed situations, thermal plastic bonding of the vent to the pouch may be the more preferred mounting technique.

Figures 4A, 5:
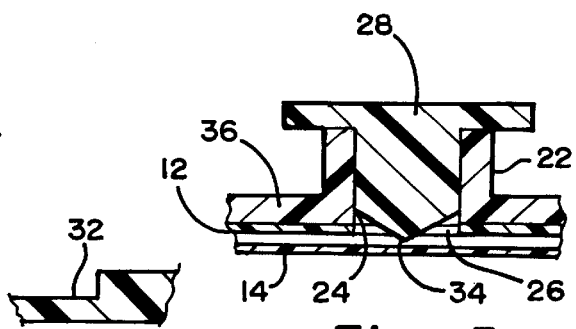
FIG. 4A is an enlarged fragmentary view further illustrating the circled portion of FIG. 4 indicated.
FIG. 5 is a further enlarged, fragmentary, sectional view showing the vent structure in a closed position.
Figure 4:
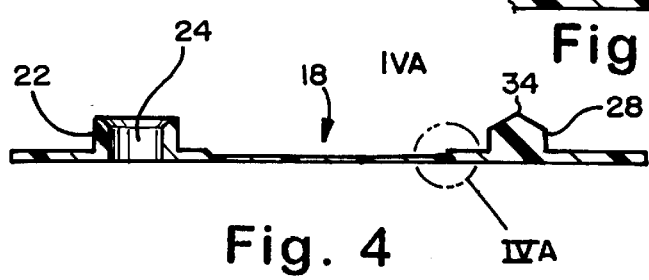
FIG. 4 is a sectional side elevational view taken through the plane IV—IV of FIG. 3.

As noted above, the plug-like closure member 28 preferably has a pointed or other such projection 34 at its outermost end, to serve as a clean-out or vent-opening device in instances where material from within the pouch clogs or obscures the opening 26 extending through side 12 of the pouch and/or the entrance to passage 24 in tubular/annular member 22. This relationship is generally illustrated in FIG. 5, wherein the closure member 28 is shown in its fully inserted position. As shown there, the length of the plug-like member 28 is preferably such as to position the end extremity 34 through and at least slightly beyond the end of passage 24 in tubular member 22, and partially through the opening 26 in pouch side 12, slightly into the interior of the pouch (but preferably not bearing against the rear side 14 thereof). As will be appreciated from this relationship, the extended end portion 34 of plug 28 will tend to prevent any buildup of material within the pouch at the entrance to the vent opening, and will also tend to break up and dislodge any such buildup as may occur when the closure member is either inserted into or withdrawn from the vent. In this regard, it is to be noted that the pointed shape of projection 34 illustrated and described herein merely represents one of several possible configurations which may be useful for this clean-out purpose, even though it is the preferred configuration presently contemplated. Since it is, of course, important that the pointed end extremity 34 not rupture the rear side 14 of the pouch, it is desirable that the point not be particularly sharp or that the material forming the closure not be so hard as to promote undue abrasion leading to such rupture.

Although evident from the drawings and the remarks made above, it will be appreciated that the portion of the vent device 18 surrounding the plug-like closure member 28 also desirably forms a generally flat skirt-like portion 38, which provides a convenient tab that may be readily grasped by the user to open the vent when this is desired, and also to close the vent. Of course, it is important that the vent remain closed in a secure and reliable manner during use, unless and until it is intentionally opened, and the frictional engagement of the plug-like closure 28 into the passage 24 of tubular/annular member 22 is therefore of definite importance, such engagement preferably being of a "press-fit" nature, i.e., an interference fit between the two parts, preferably involving at least some resilient deformation of one or the other, or each, such part.

As will now be appreciated, the present invention provides a simple but effective and reliable apparatus by which colostomy pouches may optionally be made ventable by the user, on an as-needed basis, without risk of premature and undesired detachment of the pouch from its mounting, as would likely occasion disastrous spilling of some or all of the contents. As the above description and attached drawings show, the preferred embodiment preferably does not include any element (including filter elements) extending across the vent opening other than the releasable closure, to ensure that the vent opening will function properly when desired and not become clogged, etc. In this connection, the preferred extension of the closure member provides a desirable clean-out function for ensuring that the vent opening remains clear and functional. Of course, if the closure member clean-out extension is omitted, the closure member can still function as a reliable seal and a filter or other element may be used inwardly of the closure member.

It is to be pointed out once again that while the foregoing disclosure addresses a particular preferred embodiment, and best mode, the particular apparatus described and the various detailed aspects thereof noted are regarded as pertaining to only the most preferred version of the invention and to merely illustrate the principles and concepts involved in the invention, other embodiments and versions of the invention no doubt being feasible and potentially appropriate in other circumstances. It is therefore to be understood that the foregoing description of a particular preferred embodiment is provided for purposes of description and illustration, and not as a measure of the invention, whose scope is to be defined solely by reference to the ensuing claims. Embodiments of the invention differing from those set forth above which nonetheless utilize the underlying concepts of the invention and incorporate its spirit should therefore be considered as within the scope of the claims appended below, unless such claims by their language specifically state otherwise.

The embodiments of the invention in which an exclusive property or privilege is claimed are defined as follows:

1. A vented colostomy pouch comprising in combination:
    an envelope-like container of thin, flexible waterproof material having a pair of opposite sides and upper and lower portions;
    a waste aperture adapted to receive waste matter from a wearer;
    a vent aperture extending through one of said sides at a location in the upper portion of said container;
    an open-centered generally annular member secured to an exterior surface of said one of said sides in a position generally encircling said vent aperture to form a vent opening; and
    a plug-type closure member releasably and removably retained within said annular member to seal said vent opening, such that removal of said closure member vents the interior of said container through said opening and replacement of said closure member closes and reseals said opening.

2. A vented colostomy pouch as recited in claim 1, wherein at least one of said annular member and said closure member are formed of resilient material so as to resiliently flex during placement of said closure member in said annular member.

3. A vented colostomy pouch as recited in claim 1, wherein said annular member includes a central generally tubular portion for receiving said closure member and a thin skirt portion extending radially from said tubular portion for securing the annular member to said one of said sides of said container.

4. A vented colostomy pouch as recited in claim 3, including an adhesive attachment between said skirt portion and said one of said sides.

5. A vented colostomy pouch as recited in claim 3, wherein said skirt portion has a rounded peripheral edge.

6. A vented colostomy pouch as recited in claim 4, including an attachment between said closure member and said generally annular member, whereby each of said members is part of a unitary element.

7. A vented colostomy pouch comprising in combination:
    an envelope-like container of thin, flexible waterproof material having a pair of opposite sides and upper and lower portions;
    a waste aperture adapted to receive waste matter from a wearer;
    a vent aperture extending through one of said sides at a location in the upper portion of said container;
    an open centered generally annular member secured to said one of said sides in a position generally encircling said vent aperture to form an enlargement thereof constituting a vent opening, said annular member including a central generally tubular portion for receiving a closure member and a thin skirt portion extending radially from said tubular portion, the skirt portion being attached to said one of said sides so as to secure the annular member to said one of said sides of said container;
    a plug-type closure member releasably and removably retained within said annular member to seal said vent opening such that removal of said closure member vents the interior of said container through said opening, and replacement of said closure member closes and reseals said opening; and
    an attachment between said closure member and said generally annular member, whereby each of said members is part of a unitary element, said attachment being flexible in at least selected areas to permit movement of said closure member outward and away from said generally tubular portion by flexing of said at least selected areas.

8. A vented colostomy pouch as recited in claim 7, wherein the annular member, closure member and attachment are integrally molded from a moldable plastic material, and said attachment includes an integral hinge at said selected area, said integral hinge comprising a flexible portion of plastic material interconnecting the closure member and the annular member.

9. A vented colostomy pouch comprising in combination:
    an envelope-like container of thin, flexible waterproof material having a pair of opposite sides and upper and lower portions;
    a waste aperture adapted to receive waste matter from a wearer;
    a vent aperture extending through one of said sides at a location in the upper portion of said container;
    an open centered generally annular member secured to one of said sides in a position generally encircling said vent aperture to form an enlargement thereof constituting a vent opening;
    said annular member including a central generally tubular portion for receiving a closure member and a thin skirt portion extending radially from said tubular portion, the skirt portion being attached to said one of said sides so as to secure the annular member to said one of said sides of said container; and
    a plug-type closure member releasably and removably retained within said annular member to seal said vent opening such that removal of said closure member vents the interior of said container through said opening and replacement of said closure member closes and reseals said opening said closure member having an effective length which is at least slightly greater than the axial length of said tubular member, whereby said closure member extends at least slightly through and beyond said tubular member when fully inserted therein.

10. A vented colostomy pouch as recited in claim 9, wherein said closure member has a generally pointed end extremity by which it is insertable into and at least slightly through said tubular member to clear said aperture of obstructing material.

11. A colostomy pouch comprising:

an enclosed bag formed of a waterproof flexible sheet material, the bag having an inlet opening that is adapted to be mounted over an opening in a user's body for receipt of bodily waste into the bag, the bag also having a vent aperture through the sheet material;

a manually operable vent mechanism for the pouch comprising;

an annular member sealingly mounted on the bag over the vent aperture, the annular member including a vent opening therethrough in communication with the vent aperture, with a resilient peripheral surface of the annular member surrounding the vent opening;

a plug that sealingly engages the vent opening from an exterior side thereof, the plug resiliently engaging the peripheral surface of the annular member with a frictional fit that resists axial dislodgment of the plug, the frictional fit between the plug and annular member being sufficiently secure that the plug remains in sealing engagement with the annular member until it is manually removed, the plug having a gripping portion thereof that can be manually manipulated to remove the plug from the opening in the annular member for venting the bag.

12. A colostomy pouch according to claim 11 wherein the plug and annular member are connected together by a flexible connector that permits the plug to be inserted and removed from the opening in the annular member without becoming detached from the annular member.

13. A colostomy pouch according to claim 12 wherein the annular member, plug, and connector comprise a unitary element integrally formed from a flexible moldable material.

14. A colostomy pouch according to claim 11 wherein the annular member includes an elongated, generally cylindrical interior opening that is in axial alignment with the vent aperture, the annular member further comprising an enlarged, generally flat skirt extending radially outwardly from the annular member at an end thereof adjacent the bag, the skirt being sealingly bonded to the bag, the plug being an elongated member that mates with and fits securely in the interior opening in the annular member, the plug having elongated, substantially non-tapered sides that fit snugly in the interior opening in the annular member with sufficient friction to resiliently restrain removal of the plug from the annular member without intentional manual manipulation of the plug.

15. A colostomy pouch according to claim 14 wherein the interior opening in the annular member has elongated walls that are generally parallel to the axis of the interior opening and the walls are resiliently expandable in a radial direction, the plug comprising exterior walls that are generally parallel to the axis of the plug, a resilient engagement between the plug and annular portion being sufficient to hold the plug in the interior opening under normal circumstances of pouch use until the plug is removed from the interior opening in an axial direction.

16. A colostomy pouch according to claim 15 wherein the plug comprises a manually grippable flap adjacent an outer portion thereof that can be gripped for pulling the plug out of the interior opening in the annular member.

17. A colostomy pouch according to claim 11 wherein the annular member is bonded to the bag by a pressure sensitive adhesive, a grip of the adhesive being sufficiently strong to hold the annular member on the bag but permitting the annular member to be peeled off the bag for replacement or re-use on another bag.

18. A colostomy pouch according to claim 11 wherein the annular member is permanently and non-removably bonded to the bag.

* * * * *